US00PP08749P

United States Patent [19]

Bartels

[11] Patent Number: Plant 8,749

[45] Date of Patent: May 24, 1994

[54] ASTER PLANT NAMED WHITE MASTER

[75] Inventor: G. B. H. Bartels, Hornweg 53, 1432 GD Aalsmeer, Netherlands

[73] Assignee: G. B. H. Bartels, Aalsmeer, Netherlands

[21] Appl. No.: 86,143

[22] Filed: Jul. 6, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—G. B. H. Bartels

[57] ABSTRACT

A distinct cultivar of aster plant named White Master, characterized by its large inflorescences, large number of ray and disc florets, wide and long leaves, and dense inflorescence arrangement.

1 Drawing Sheet

The present invention relates to a new and distinctive cultivar of Aster hybrid, hereinafter referred to by the cultivar name White Master.

The new cultivar was developed by me at Bartelstek, Aalsmeer, Holland, through controlled breeding by crossing the cultivar identified as 88-287 white as the female parent with the cultivar identified as 88-273 white as the male parent. Both parents are hybrids of aster cultivars, species unknown.

Asexual reproduction of the new cultivar by terminal or stem cuttings taken at Aalsmeer, Holland, has shown that the unique features of this new aster are stabilized and are reproduced true to type in successive generations of asexual reproduction.

The following characteristics distinguish the new aster from both its parent varieties and other cultivated asters of this type known and used in the floriculture industry:

1. White Master has large inflorescences which are distinctive.
2. White Master has more ray florets per inflorescence than comparable cultivars.
3. Leaves of White Master are longer and wider than comparable cultivars.
4. White Master plants have a denser inflorescence arrangement.

The accompanying colored photographs illustrate the overall appearance and flower color of the new cultivar, showing the colors as true as it is reasonably possible to obtain in colored reproduction of this type. The photograph is a single flowering stem of White Master.

The new cultivar can be compared in certain characteristics to the nonpatented cultivar Monte Casino. In general comparison to Monte Casino, White Master has:

1. Larger inflorescences, two times larger in diameter than Monte Casino.
2. More ray and disc florets, on average 1.5 times more ray and disc florets giving fuller inflorescences than Monte Casino.
3. Shorter lateral stems which give White Master a denser inflorescence arrangement compared to Monte Casino's more open inflorescence arrangement.
4. White Master has leaves that are two times as wide and two times as long as leaves of Monte Casino.

The following is a detailed description of my new cultivar based on plants produced under normal commercial practice in Aalsmeer, Holland, in a glass-covered greenhouse with day temperatures of 16° to 18° C.

and night temperatures of 12° C. during the vegetative phase and day temperatures of 22° to 25° C. and night temperatures of 18° C. during the flowering phase.

Color references are made to The Royal Horticultural Society Colour Chart except where general terms of ordinary dictionary significance are used.

Botanical classification: Aster hybrid cv White Master.

Parentage:

*Male parent.*—Bartelstek 88-273 white.

*Female parent.*—Bartelstek 88-287 white.

Propagation:

A. *Type.*—By terminal tip cuttings, tissue culture and division.

B. *Time to initiate roots.*—14 days at 25° C. during the summer.

C. *Time to initiate roots.*—20 days at 20° C. during the winter.

D. *Rooting habit.*—Fibrous, branching.

Plant description:

A. *General appearance.*—Upright, freely branching and vigorous.

B. *Foliage description.*—Shape: Linear, elongated, narrow. Size. 10.5 cm in length, 0.4 cm in width. Texture: Smooth, not pubescent. Margin: Entire. Color: Young foliage top side: 147A. Young foliage under side: 147A. Mature foliage top side: 147A. Mature foliage under side: 147A. Venation: Parallel, branched, color is 147A.

Flowering description:

A. *Flowering habit.*—Panicles of florets, radiate capitula.

B. *Natural flowering season.*—Natural flowering season is the fall in the northern hemisphere.

C. *Quantity of flowers.*—More than ten inflorescences on each lower flowering lateral stem and more than 150 inflorescences per each harvested stem.

D. *Ray florets.*—Shape: Ligulate. Color: Top side: 155D. When opening: 155D. Fading to: 155D. Under side: 155D. Number of ray florets: 28 to 32 ray florets per inflorescence. Size of inflorescence: 2.5 cm in diameter.

E. *Disc florets.*—Shape: Tubular. Color: Color mature: 6C. Color immature: 6A. Number of disc florets: 28 to 32 per inflorescence. Diameter of disc: 0.75 cm.

F. *Reproductive organs.*—Stamens: Anther color: 9C. Pollen color: 9C. Pistils: Stigma color: 6D. Style color: 144C.

Disease resistance: No fungal or bacterial problems observed to date.

I claim:

1. A new and distinct cultivar of aster plant named White Master, as illustrated and described.

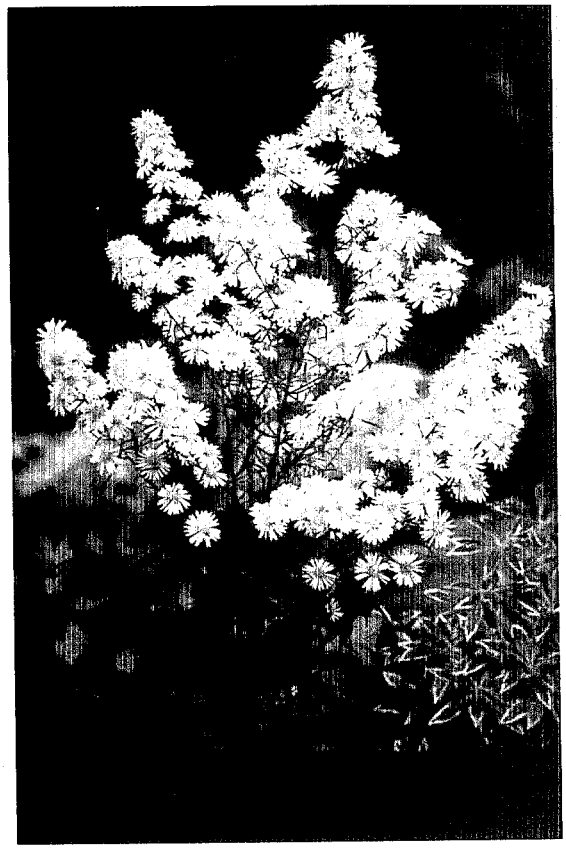

* * * * *